US012758385B2

(12) United States Patent
Lv et al.

(10) Patent No.: US 12,758,385 B2
(45) Date of Patent: Oct. 13, 2026

(54) INTEGRALLY DETACHABLE VALVE CLAMP AND DELIVERY SYSTEM THEREOF

(71) Applicant: JENSCARE SCIENTIFIC CO., LTD, Ningbo (CN)

(72) Inventors: Shiwen Lv, Ningbo (CN); Zhi Chen, Ningbo (CN); Kan Lu, Ningbo (CN); Lei Wu, Ningbo (CN)

(73) Assignee: JENSCARE SCIENTIFIC CO., LTD, Ningbo (CN)

( * ) Notice: Subject to any disclaimer, the term of this patent is extended or adjusted under 35 U.S.C. 154(b) by 665 days.

(21) Appl. No.: 18/257,584

(22) PCT Filed: Nov. 26, 2021

(86) PCT No.: PCT/CN2021/133490
§ 371 (c)(1),
(2) Date: Jun. 14, 2023

(87) PCT Pub. No.: WO2022/127562
PCT Pub. Date: Jun. 23, 2022

(65) Prior Publication Data

US 2024/0115386 A1 Apr. 11, 2024

(30) Foreign Application Priority Data

Dec. 18, 2020 (CN) ......................... 202011506767.3

(51) Int. Cl.
*A61F 2/24* (2006.01)

(52) U.S. Cl.
CPC ............ *A61F 2/246* (2013.01); *A61F 2/2466* (2013.01)

(58) Field of Classification Search
CPC ...... A61F 2/246; A61F 2/2466; A61F 2/9517; A61F 2/2442; A61B 17/08; A61B 17/10; A61B 17/122
See application file for complete search history.

(56) References Cited

U.S. PATENT DOCUMENTS

2019/0261997 A1 8/2019 Goldfarb et al.

FOREIGN PATENT DOCUMENTS

CN 110664515 A 1/2020
CN 211325891 U 8/2020
CN 111671547 A 9/2020
(Continued)

OTHER PUBLICATIONS

Office Action and its Search Report with English translation of Chinese patent application No. 202011506767.3 dated Dec. 26, 2024, 18 pages.

(Continued)

*Primary Examiner* — Yashita Sharma
(74) *Attorney, Agent, or Firm* — Syncoda LLC; Feng Ma

(57) ABSTRACT

An integrally detachable valve clamp and delivery system thereof includes a control handle, a delivery catheter connected to the control handle, and a valve clamp connected to the delivery catheter, wherein the valve clamp is equipped with an inner catheter and an outer catheter, both of which are equipped with detachable connection mechanisms; the delivery catheter comprises a first delivery catheter, a central control unit, and a second delivery catheter; the distal parts of both the first delivery catheter and the second delivery catheter are equipped with releasable connection mechanisms that match the detachable connection mechanisms.

10 Claims, 25 Drawing Sheets

(56) References Cited

FOREIGN PATENT DOCUMENTS

| | | | |
|---|---|---|---|
| CN | 211560531 | U | 9/2020 |
| CN | 111870398 | A | 11/2020 |
| CN | 113509291 | A | 10/2021 |
| CN | 214511423 | U | 10/2021 |
| CN | 214596110 | U | 11/2021 |

OTHER PUBLICATIONS

International Search Report with English translation for PCT/CN2021/133490 dated Feb. 28, 2022, 8pages.

INTEGRALLY DETACHABLE VALVE CLAMP AND DELIVERY SYSTEM THEREOF

CROSS-REFERENCE TO RELATED APPLICATIONS

The present application is a National Stage of International Application No. PCT/CN2021/133490 filed on Nov. 26, 2021, which claims priority to Chinese patent application number 202011506767.3 filed on Dec. 18, 2020. The disclosures of the above-referenced applications are hereby incorporated by reference in their entirety.

TECHNICAL FIELD

The present application relates to the field of medical equipment, and particularly relates to an integrally detachable valve clamp and delivery system thereof.

BACKGROUND

The anatomical structure of a mitral valve is complex, including valve leaflet, valve annulus, chordae tendineae and papillary muscle, which play an important role in maintaining left and right ventricle function. Any disease that affects the structural integrity and normal function of valve leaflet, valve annulus, chordae tendineae, papillary muscle, and left ventricle can lead to severe mitral regurgitation (MR), which can cause left ventricular failure, pulmonary hypertension, atrial fibrillation, stroke, and death. According to the latest epidemiological survey data of the United States and other western developed countries, mitral valve reflux is the type of valvular disease with the highest incidence rate among the elderly over 65 years of age. At present, although there is no authoritative epidemiological survey data in China, there is no doubt about the large number of patients with mitral valve reflux as the population ages. Mitral regurgitation can be divided into degenerative MR and functional MR. Degenerative MR is caused by pathological changes in one or more of the valve leaflet, valve annulus, chordae tendineae and papillary muscle, and functional MR is usually characterized by left ventricle dysfunction, such as valve annulus enlargement, but the mitral valve is usually normal.

At present, the treatment methods for MR mainly include medication, surgery, and interventional therapy. Medication can only improve patients' symptoms and cannot extend patients' survival time. Surgery, mainly valve repairment or valve replacement, are widely recognized as the preferred treatment for mitral valve reflux and have been proven to alleviate symptoms and prolong patients' life. However, for many high-risk patients with advanced age and multiple system diseases, the surgery risk is high and the survival benefits are limited. According to European data, the surgery success rate of such patients is only 50%, and the surgery success rate of severe functional MR patients is as low as 16%. Therefore, transcatheter intervention mitral valve repairment and replacement can theoretically benefit high-risk patients who have lost the opportunity for surgical surgery. Interventional therapy involves loading an artificial implant onto a delivery system in vitro, delivering it to the mitral valve annulus along a vascular pathway or through a cardiac puncture, and then releasing and fixing it to completely or partially replace the function of the autologous valve. Currently, mitral valve intervention therapy has become one of the hot research topics in related fields, and many products are being developed. However, due to the complexity of the mitral valve itself and its surrounding structure, the development of mitral valve intervention instruments faces many special difficulties.

The Chinese patent application No. 201280044346.0 disclose a method for fixing tissues, comprising: providing an implantable fixing device, which comprises a pair of fixing elements, each of the fixing elements has a first end, a free end opposite the first end, and a buckle surface located between the first end and the free end to bind the tissue. The first ends are movably connected together, enabling the fixed components to move between the closed position and the first open position. In the closed position, the buckle surfaces face each other, while in the first open position, the buckle surfaces are far away from each other. The detachable connection structure between the conveying system and the valve clamp is relatively complex, which may cause difficulties in release during actual operation.

The Chinese patent application No. CN201880066104.9 discloses a valve clamp device comprising a spacer component configured to be arranged between the leaflets of a natural heart valve located between the first and second chambers of the heart. A prosthetic device further includes multiple anchoring components, which are coupled to the spacer component and configured to capture the leaflets between their respective anchoring components and the spacer component, so that the prosthetic device is maintained between the leaflets. When the leaflets are captured between the anchoring components and the spacer component, the spacer component is configured to provide a flow path through the prosthetic device between the first and second cavities, allowing blood to flow back from the second cavity to the first cavity through the spacer component. After the valve clamp is implanted in the target position in the present application, the delivery system needs to first rotate the inner tube to separate it from the threads on the valve clamp, then evacuate the inner tube towards the proximal end, and then move the detachable component towards the proximal end to separate it from the valve clamp. The operation steps are relatively cumbersome, and at the same time, the structural design of detachable components is complex, requiring high assembly process requirements and making implementation difficult.

In conclusion, the disassembly and connection structure design between the conveying system and the valve clamp in prior art is relatively complex, which has high assembly process requirements. Meanwhile, the complex structure further makes the operation process cumbersome.

SUMMARY

The advantage of the present application is to provide an integrally detachable valve clamp and delivery system thereof, which has the following advantages: a delivery catheter passes through the inferior vena cava and atrial septum during the delivery of a valve clamp without damaging the heart tissue, a first delivery catheter and a second delivery catheter provide support for the movement of the valve clamp in the heart, and the first and second delivery catheters are detached from the valve clamp after completing the clamping and locking of the valve leaflets, reducing the burden of the valve clamp on the heart, enabling valve clamp to better maintain the clamping state of the valve leaflets.

The above technical problems can be solved through the following technical solutions:

A component of an integrally detachable valve clamp and delivery system thereof comprises a control handle, a delivery catheter connected to the control handle, and a valve clamp connected to the delivery catheter; the valve clamp is equipped with an inner catheter and an outer catheter, both of which are equipped with detachable connection mechanisms; the delivery catheter comprises a first delivery catheter, a central control unit, and a second delivery catheter; the distal parts of both the first delivery catheter and the second delivery catheter are equipped with releasable connection mechanisms that match the detachable connection mechanisms; when pre-installed, the detachable connection mechanism on the inner catheter is connected to the releasable connection mechanism on the first delivery catheter through the central control unit, forming a first disassembly part, while the detachable connection mechanism on the outer catheter is connected to the releasable connection mechanism on the second delivery catheter through the central control unit, forming a second disassembly part; when the central control unit is moved away from the first disassembly part and the second disassembly part, the first delivery catheter separates from the inner catheter, and the second delivery catheter separates from the outer catheter.

The objectives of the present application may also be further realized by following technical solutions;

In an embodiment, the valve clamp further comprises a connector, a first clamping arm, a second clamping arm, a first linkage rod, and a second linkage rod; the first clamping arm and the second clamping arm are hinged with the connector and are arranged on the left and right sides of the outer catheter; the connector is connected to the inner catheter; one end of the first linkage rod is connected to the first clamping arm, while the other end of the first linkage rod is connected to the outer catheter; and one end of the second linkage rod is connected to the second clamping arm, while the other end of the second linkage rod is connected to the outer catheter In an embodiment, when the first disassembly part and the second disassembly part undergo relative displacement, the relative position of the central control unit and the inner catheter remains unchanged; when the first disassembly part and the second disassembly part undergo relative displacement, the opening and closing of the valve clamp can be controlled, while the relative position of the central control unit and the inner catheter remains unchanged to ensure that the valve clamp is not disassembled in advance during the opening and closing process; Meanwhile, the central control unit fills a gap between the first delivery catheter and the inner catheter, and a gap between the second delivery catheter and the outer catheter, making the entire device more stable during operation.

In an embodiment, the central control unit restricts the relative radial displacement between the detachable connection mechanisms and the releasable connection mechanisms to prevent the detachable connection mechanisms from detaching from the releasable connection mechanisms.

In an embodiment, when the releasable connection mechanisms are connected to the detachable connection mechanisms, the outer peripheral surfaces of the first disassembly part and the second disassembly part are closed.

In an embodiment, each of the detachable connection mechanisms includes a first connection section, a second connection section, and an inclined section, and the inclined section is set between the first connection section and the second connection section; the inclined section can make the detachable connection mechanisms and the releasable connection mechanism more smooth during disassembly and separation, effectively avoiding unnecessary hooking between the two during the disassembly process, which will lead to separation failure.

In an embodiment, the inclined section includes a inclined plane, and the angle between the inclined plane and the central axis of the inner catheter is between 0° and 90°.

In a preferred embodiment, the smaller the angle between the inclined plane and the central axis of the inner catheter, the smoother the disassembly of the detachable connecting mechanisms with the releasable connecting mechanisms.

In an embodiment, the central control unit is a tube, the wall thickness of which is greater than or equal to half of the radial distance between the first connection section and the second connection section on the detachable connection mechanism of the inner catheter, and the advantage of this is that it can avoid interference when the detachable connection mechanism of the inner catheter is separated from the releasable connection mechanism of the first delivery catheter.

In an embodiment, the detachable connection mechanisms and the releasable connection mechanisms have a central symmetric relationship, and the advantage of this is that the detachable connection mechanisms are more tightly connected to the releasable connection mechanisms, and the connection between the two is more stable and reliable.

In an embodiment, when the releasable connection mechanisms are connected to the detachable connection mechanisms through the central control unit, the first delivery catheter and the second delivery catheter can respectively transmit torque and push force to the inner catheter and the outer catheter.

In an embodiment, on the axial section of the delivery catheter, the first disassembly part and the second disassembly part are in the same or different positions.

In another embodiment, the detachable connection mechanisms and the releasable connection mechanisms are in a "LI (concave)", "1 (convex)", "U" or other shapes.

In another embodiment, the detachable connection mechanism of the inner catheter is naturally in an outward expansion state, while the detachable connection mechanism of the outer catheter is naturally in a folded state.

In an embodiment, the inner catheter comprises a self-locking rod and a locking head connected to the connector; the clamping arm comprises a long arm and a short arm, and one end of the short arm is provided with a locking part; when the inner catheter is axially moved to enlarge the angle between the long arm of the first clamping arm and the long arm of the second clamping arm to an open state, the locking part on the first clamping arm and the second locking part on the second clamping arm are in a staggered fit state; when the inner catheter is moved axially to reduce the angle between the long arm of the first clamping arm and the long arm of the second clamping arm to a closed state, the self-locking rod is moved to achieve matching and locking between the locking head and the locking part.

In an embodiment, the locking head is a bracket shaped self-expanding structure, which cooperates with the locking part to achieve locking.

In a preferred embodiment, the self-locking rod is a solid rod, and the advantage of this is that it enhances the strength of the inner catheter and prevents the valve clamp from breaking between the detachable connection mechanism of the inner catheter and the releasable connection mechanism on the first delivery catheter during the locking process, resulting in locking failure.

In another embodiment, the self-locking rod can be a hollow rod, which can reduce the weight of the entire valve clamp device.

In an embodiment, the inner catheter, the outer catheter, the central control unit, the connector, the clamping arm, and the linkage rod are all made of rigid materials, and the advantage of this is that when the central control unit and the outer catheter move axially, the entire structure of the implanted prosthesis has good support and will not deform during operation, which is conducive to surgical operations; on the other hand, it can ensure long-lasting clamping force and will not cause fatigue and other problems.

The advantages of the present application over the prior art are:

1. Unlike prior art, when pre-installing the delivery system of the present application, the central control unit limits the relative radial displacement between the releasable connection mechanisms and the detachable connection mechanisms to prevent the releasable connection mechanisms from detaching from the detachable connection mechanisms, while when operating the central control unit to leave the first disassembly part and the second disassembly part, the releasable connection mechanisms lose their circumferential position limitation, which will enable the first disassembly part and the second disassembly part separate step by step/synchronously; this structural design is simple and very clever, which can dismantle the two connecting structures one by one/simultaneously by only moving the central control unit.
2. Unlike prior art, the detachable connection mechanisms and the releasable connection mechanisms in the present application have a central symmetric relationship, which enable the connection between the detachable connection mechanisms and the releasable connection mechanisms more tightly, and the connection between the two is more stable and reliable.
3. Unlike prior art, the present application has an inclined section, which makes the detachable connection mechanisms and the releasable connection mechanisms smoother during disassembly and separation, effectively avoiding accidents that cannot be separated normally due to unnecessary hooking or interference between the two during the disassembly process.
4. Unlike prior art, when the opening angle between the first clamping arm and the second clamping arm in the present application increase, the locking part on the first clamping arm and the locking part on the second clamping arm are misaligned connected, which does not interfere/affect the opening angle between the clamping arms and is conducive to capturing and clamping the valve leaflets; when the valve clamp needs to be locked, the inner catheter moves axially towards the distal end along the connector until one end of the inner catheter completes the locking fit with the fixed area, that is, completing the lock; by utilizing the lever principle, a torque balance is generated between the locking head and the locking parts, controlling the angle between the first clamping arm and the second clamping arm to no longer increase, achieving the locking effect; meanwhile, the locking structure is mechanically locked, with a simple structure, easy operation, and no risk of fatigue, which can ensure its clamping effect for a long time.
5. Unlike prior art, when the first disassembly part and the second disassembly part undergo relative displacement, the opening and closing of the valve clamp can be controlled, while the relative position of the central control unit and the inner catheter remains unchanged to ensure that the valve clamp is not disassembled in advance during the opening and closing process. Meanwhile, the central control unit fills a gap between the first delivery catheter and the inner catheter, and a gap between the second delivery catheter and the outer catheter, making the entire device more stable during operation; after the first disassembly part is disassembled, the first delivery catheter can be withdrawn from the body along the pipeline of the central control unit.

BRIEF DESCRIPTION OF DRAWINGS

FIGS. 1A-1E are schematic diagrams illustrating the overall structure of the integrally detachable valve clamp of the present application, wherein FIGS. 1*c*-1*d* are schematic diagrams of the disassembly process of the valve clamp disassembly parts.

Figure 1A:
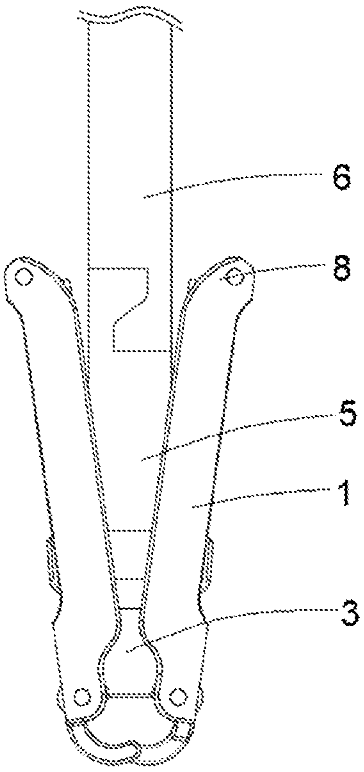

The names of the parts referred to by the numbers in the accompanying drawings are as follows: 1—clamping arm, 11—first clamping arm, 111—first locking part, 12—second clamping arm, 121—second locking part, 13—fixed area, 14—long arm, 15—short arm, 2—linkage rod, 21—first linkage rod, 22—second linkage rod, 3—connector, 31—connection block, 311—through hole, 312—installation slot, 32—connection ear, 4—inner catheter, 41—self-locking rod, 42—locking head, 43—inner detachable connection mechanism, 5—outer catheter, 51—outer detachable connection mechanism, 6—delivery catheter, 61—first delivery catheter, 62—second delivery catheter, 63—central control unit, 611—first releasable connection mechanism, 621—second releasable connection mechanism, 612—first disassembly part, 622—second disassembly part, 71—first connection section, 72—second connection section, 73—inclined section, 731—inclined plane, 8—valve clamp.

DETAILED DESCRIPTION

The present application will be further described in detail below in conjunction with the accompanying drawings and embodiments.

In the present application, the proximal end refers to the end close to the surgical operator, and the distal end refers to the end far away from the surgical operator.

Embodiment 1

An integrally detachable valve clamp and delivery system thereof, as shown in FIG. 1A to 1E, including a control handle, a delivery catheter 6 connected to the control handle, and a valve clamp 8 connected to the delivery catheter 6. The valve clamp 8 is equipped with an inner catheter 4 and an outer catheter 5, both of which are equipped with detachable connection mechanisms. The delivery catheter 6 includes a first delivery catheter 61, a central control unit 63, and a second delivery catheter 62. The distal parts of both the first delivery catheter 61 and the second delivery catheter 62 are equipped with releasable connection mechanisms that match the detachable connection mechanisms. When pre-installed, an inner detachable connection mechanism 43 on the inner catheter 4 is connected to a first releasable connection mechanism 611 on the first delivery catheter 61 through the central control unit 63, forming a first disassembly part 612. An outer detachable connection mechanism 51 on the outer catheter 5 is connected to a second releasable connection mechanism 621 on the second delivery catheter 62 through the central control unit 63, forming a second disassembly part 622. When the central control unit 63 is moved away from the first disassembly part 612 and the second disassembly part 622, the first delivery catheter 61 separates from the inner catheter 4, and the second delivery catheter 62 separates from the outer catheter 5.

The composition and connection method of each component of the detachable valve clamp 8 conveying system of the present application will be described in detail in conjunction with the accompanying drawings.

Figure 1B:
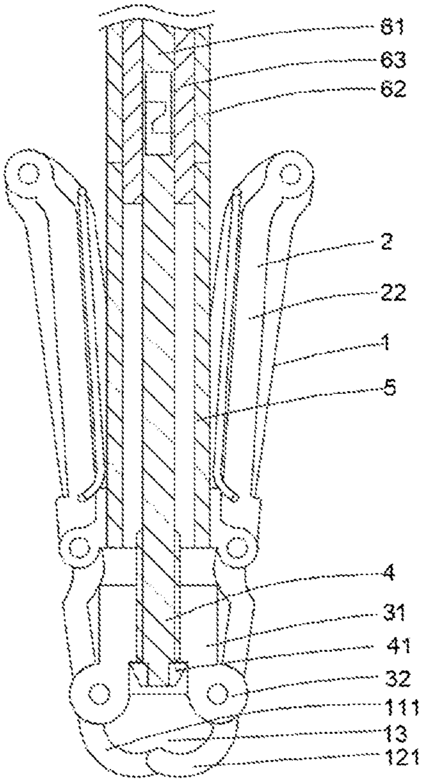

In this embodiment, as shown in FIG. 1B, the valve clamp 8 further includes a connector 3, a first clamping arm 11, a second clamping arm 12, a first linkage rod 21, and a second linkage rod 22. The first clamping arm 11 and the second clamping arm 12 are hinged with the connector 3 and are arranged on the left and right sides of the outer catheter 5. The connector 3 is connected to the inner catheter 4. One end of the first linkage rod 21 is connected to the first clamping arm 11, while the other end of the first linkage rod 21 is connected to the outer catheter 5. One end of the second linkage rod 22 is connected to the second clamping arm 12, while the other end of the second linkage rod 22 is connected to the outer catheter 5.

In this embodiment, when the first disassembly part 612 and the second disassembly part 622 undergo relative displacement, the relative position of the central control unit 63 and the inner catheter 4 remains unchanged. When the first disassembly part 612 and the second disassembly part 622 undergo relative displacement, the opening and closing of the valve clamp can be controlled, while the relative position of the central control unit 63 and the inner catheter 4 remains unchanged to ensure that the valve clamp is not disassembled in advance during the opening and closing process. Meanwhile, the central control unit 63 fills a gap between the first delivery catheter 61 and the inner catheter 4, and a gap between the second delivery catheter 62 and the outer catheter 5, making the entire device more stable during operation.

In this embodiment, the central control unit 63 restricts the relative radial displacement between the detachable connection mechanisms (referring to the inner detachable connection mechanism 43 and the outer detachable connection mechanism 51) and the releasable connection mechanisms (referring to the first releasable connection mechanism 611 and the second releasable connection mechanism 621) to prevent the detachable connection mechanisms from detaching from the releasable connection mechanisms. And when the releasable connection mechanisms (referring to the first releasable connection mechanism 611 and the second releasable connection mechanism 621) are connected to the detachable connection mechanisms (referring to the inner detachable connection mechanism 43 and the outer detachable connection mechanism 51), the outer peripheral surfaces of the first disassembly part 612 and the second disassembly part 622 are closed, as shown in FIGS. 2A to 2E.

Figure 2A:
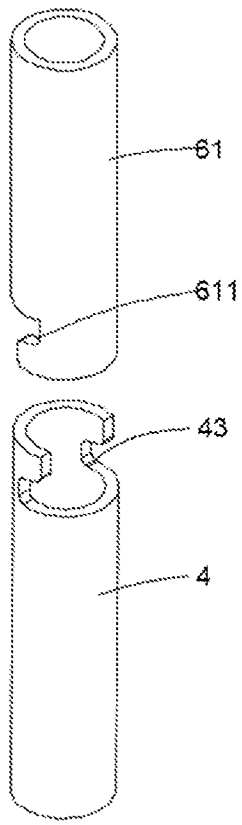
FIGS. 2A-2G are schematic diagrams illustrating the releasable connection mechanisms and detachable connection mechanisms of the present application.
Figure 2B:
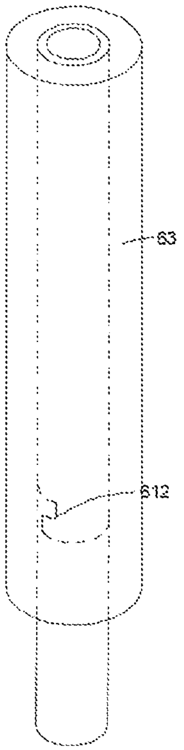
Figure 2C:
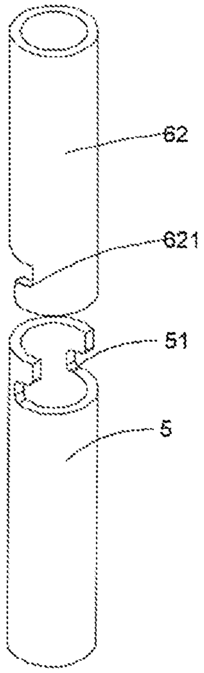
Figure 2D:
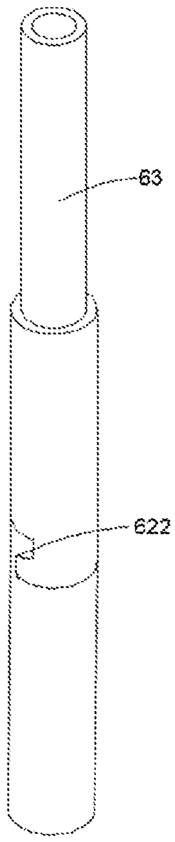
Figure 2E:
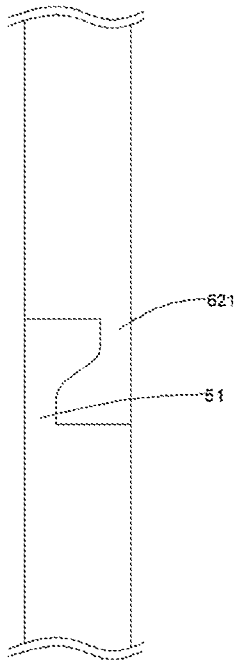
Figure 2F:
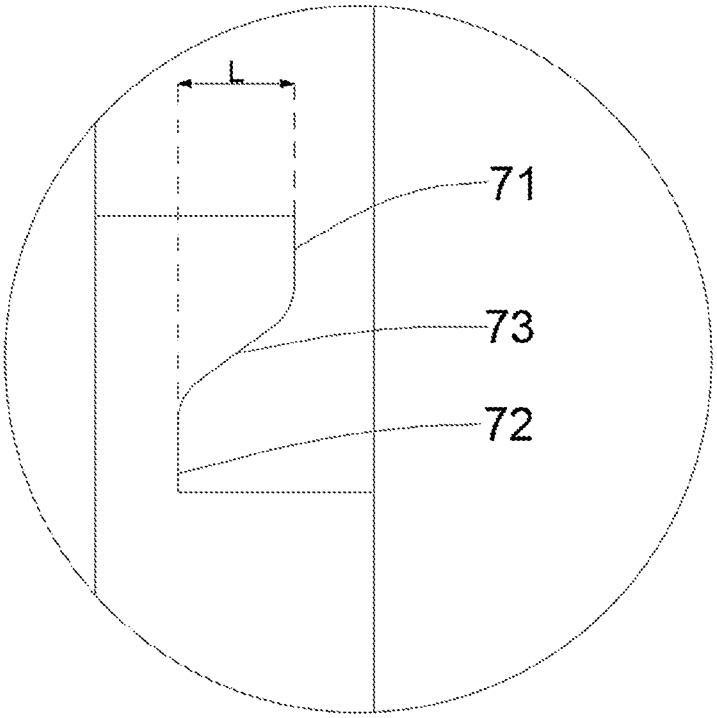

In this embodiment, each of the detachable connection mechanisms (referring to the inner detachable connection mechanism 43 and the outer detachable connection mechanism 51) includes a first connection section 71, a second connection section 72, and an inclined section 73, as shown in FIG. 2F (where L is the radial distance between the first connection section 71 and the second connection section 72), and the inclined section 73 is set between the first connection section 71 and the second connection section 72. The inclined section 73 can make the detachable connection mechanisms (referring to the inner detachable connection mechanism 43 and the outer detachable connection mechanism 51) and the releasable connection mechanism (referring to the first releasable connection mechanism 611 and the second releasable connection mechanism 621) more smooth during disassembly and separation, effectively avoiding unnecessary hooking between the two during the disassembly process, which will lead to separation failure.

Figure 1C:
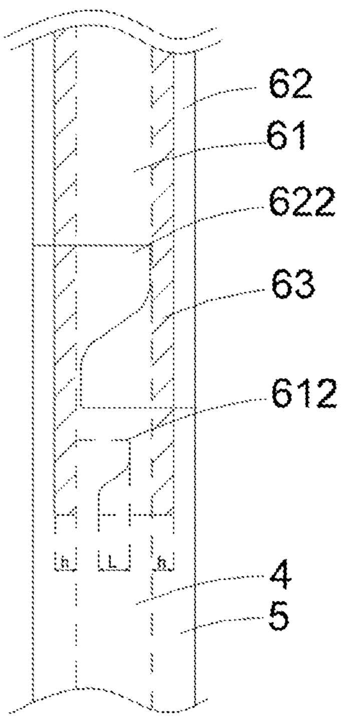

In this embodiment, the central control unit 63 is a tube, the wall thickness h of which is greater than or equal to half of the radial distance L between the first connection section and the second connection section on the detachable connection mechanism 43 of the inner catheter 4, as shown in FIG. 1C, which can avoid interference due to insufficient space when the detachable connection mechanisms (referring to the inner detachable connection mechanism 43 and the outer detachable connection mechanism 51) are separated from the releasable connection mechanisms (referring to the first releasable connection mechanism 611 and the second releasable connection mechanism 621).

Figure 2G:
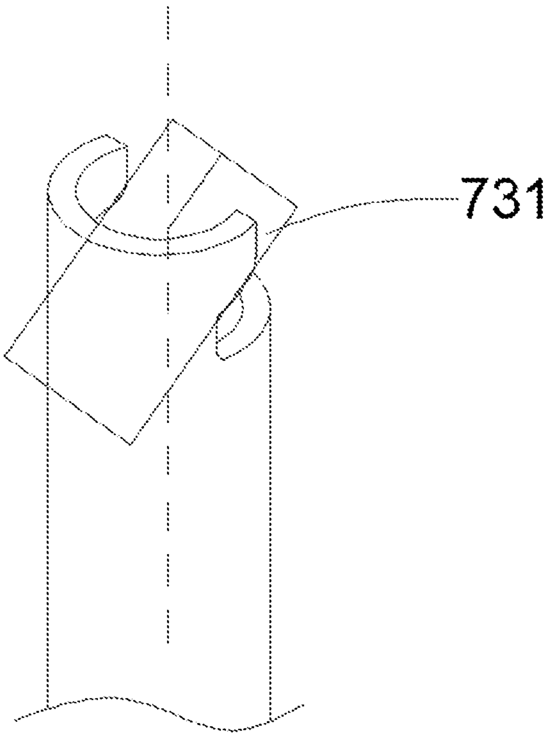

In this embodiment, the inclined section 73 includes a inclined plane 731, and the angle between the inclined plane 731 and the central axis of the inner catheter 4 is between 0° and 90°, as shown in FIG. 2G.

In this embodiment, the detachable connection mechanisms (referring to the inner detachable connection mechanism 43 and the outer detachable connection mechanism 51) and the releasable connection mechanisms (referring to the first releasable connection mechanism 611 and the second releasable connection mechanism 621) have a central symmetric relationship. As shown in FIG. 2E, so that the detachable connection mechanisms are more tightly connected to the releasable connection mechanisms, and the connection between the two is more stable and reliable.

In this embodiment, the first disassembly part 612 is located at the distal end of the second disassembly part 622. When the central control unit 63 is moved towards the proximal end, the first disassembly part 612 and the second disassembly part 622 are separated in sequence. The advantage of this is that when the first disassembly part 612 is separated from the second disassembly part 622, the releasable connection mechanisms (referring to the first releasable connection mechanism 611 and the second releasable connection mechanism 621) have sufficient separation space, and the first releasable connection mechanism 611 and the second releasable connection mechanism 621 will not interconnected with each other.

Figure 3A:
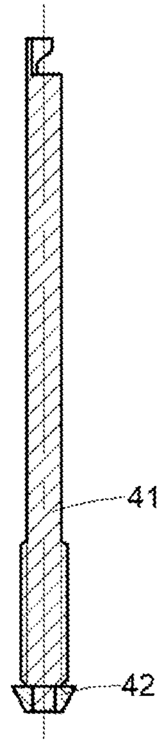
FIGS. 3A-3G are schematic diagrams illustrating the inner catheter of the present application.
Figure 4A:
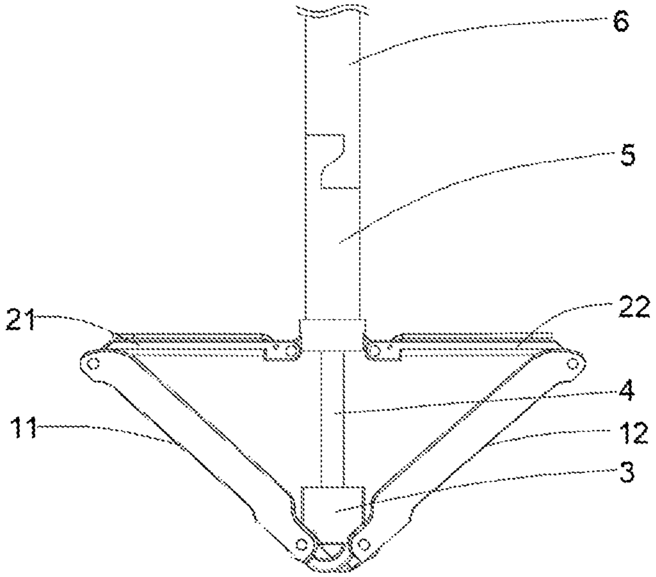
FIGS. 4A-4F are schematic diagrams illustrating relationship between various mechanisms of the present application and the structural diagram of the clamping arm.
Figure 4B:
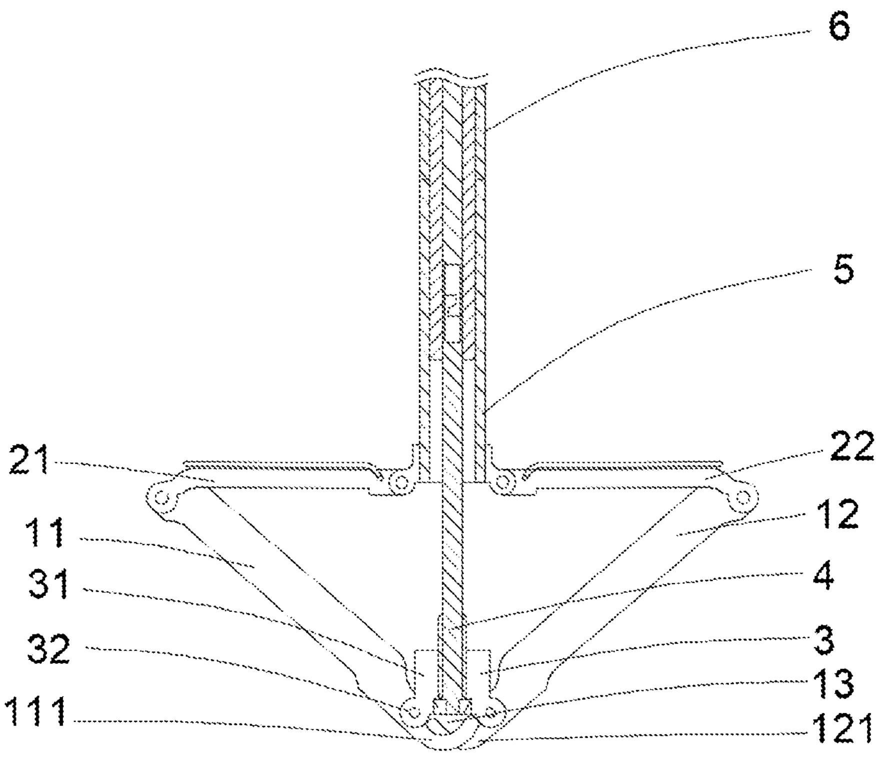
Figure 4C:
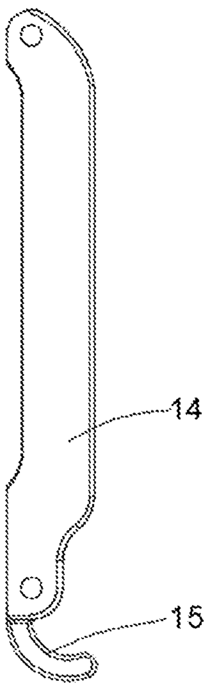
Figure 4D:
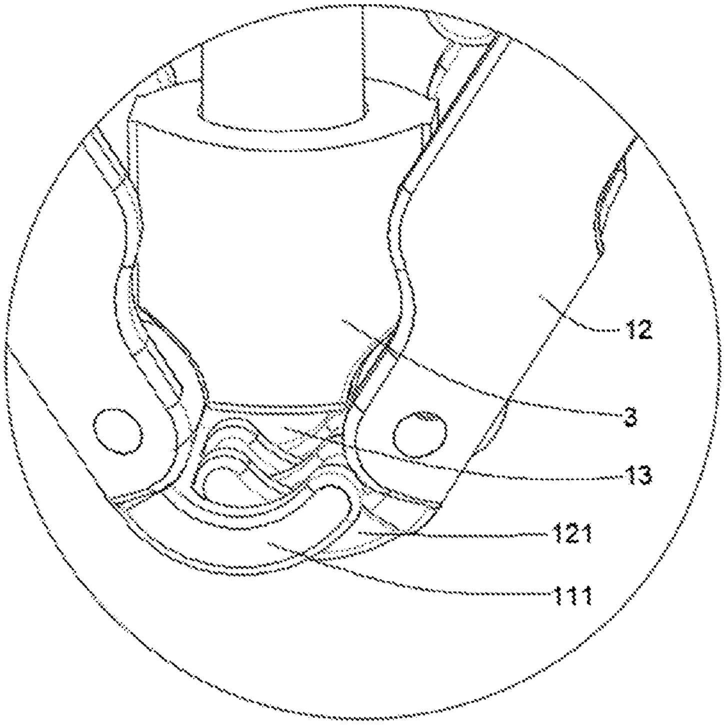
Figure 4E:
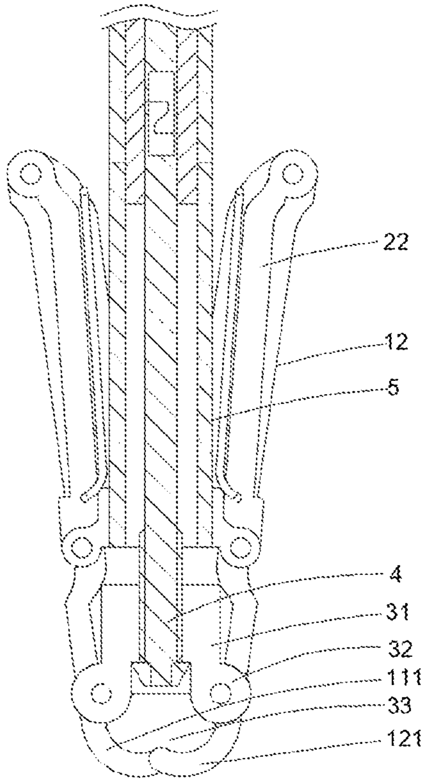
Figure 4F:
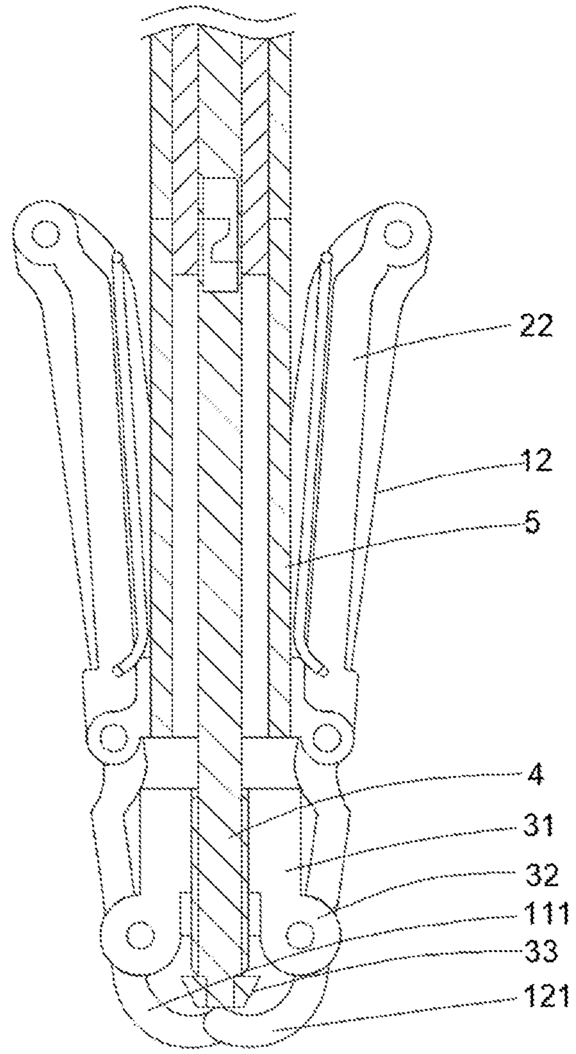

In this embodiment, the inner catheter 4 includes a self-locking rod 41 and a locking head 42 connected to the connector 3 (as shown in FIG. 3A). The clamping arm includes a long arm 14 and a short arm 15 (as shown in FIG. 4C), and one end of the short arm 15 is provided with a first locking part 111 (as shown in FIG. 4D). When the inner catheter 4 is axially moved to enlarge the angle between the long arm 14 of the first clamping arm 11 and the long arm 14 of the second clamping arm 12 to an open state, the first locking part 111 on the first clamping arm 11 and the second locking part 121 on the second clamping arm 12 are in a staggered fit state (as shown in FIGS. 4A and 4B). When the outer catheter 5 is moved axially along the inner catheter 4 to reduce the angle between the long arm 14 of the first clamping arm 11 and the long arm 14 of the second clamping arm 12 to a closed state (as shown in FIG. 4E), the self-locking rod 41 is moved to achieve matching and locking between the locking head 42 and the locking parts (referring to the first locking part 111 and the second locking part 121) (as shown in FIG. 4F). By utilizing the lever principle, a torque balance is generated between the locking head 42 and the locking parts (referring to the first locking part 111 and the second locking part 121), controlling the angle between the first clamping arm 11 and the second clamping arm 12 to no longer increase, achieving the locking effect. Meanwhile, the locking structure is mechanically locked, with a simple structure, easy operation, and no risk of fatigue, which can ensure its clamping effect for a long time.

In this embodiment, a fixed area 13 is formed between the locking parts (referring to the first locking part 111 and the second locking part 121) and the connector 3, and the locking head 42 enters the fixed area 13 and completes a locking fit with the locking parts (referring to the first locking part 111 and the second locking part 121).

In this embodiment, the locking head 42 corresponds to the fixed area 13 in a wedge-shaped structure, conical structure, trapezoidal structure, or other shape.

Figure 5A:
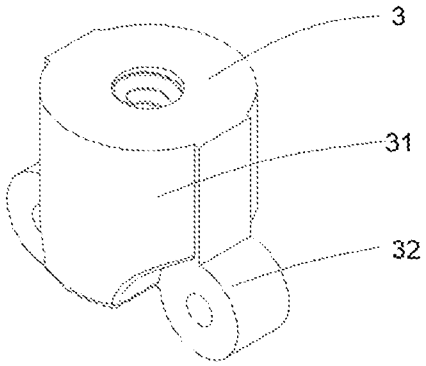
FIGS. 5A-5B are schematic diagrams illustrating the connector of the present application.
Figure 5B:
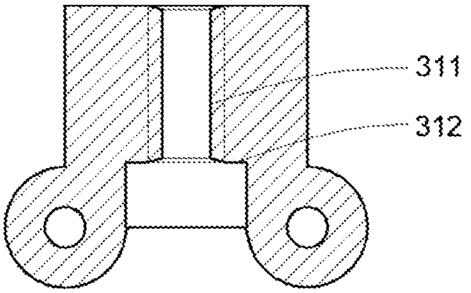

In this embodiment, the connector 3 includes a connection block 31 and connection ears 32 arranged on the connection block 31, as shown in FIGS. 5A and 5B. The connection block 31 is connected to the inner catheter 4, and the connection ears 32 are hinged with the first clamping arm 11 and the second clamping arm 12, respectively. The connection block 31 is axially provided with a through hole 311 and an installation slot 312, and the installation slot 312 is set on the distal end of the through hole 311. The through hole 311 is set with internal thread, and the distal end of the inner catheter 4 is equipped with an external thread that is matched and screwed with the internal thread.

Figure 3B:
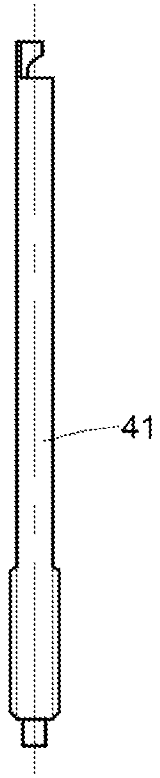
Figure 3C:
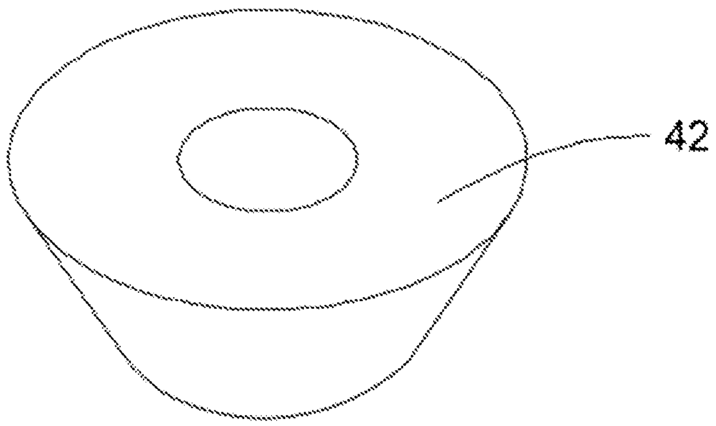
Figure 3D:
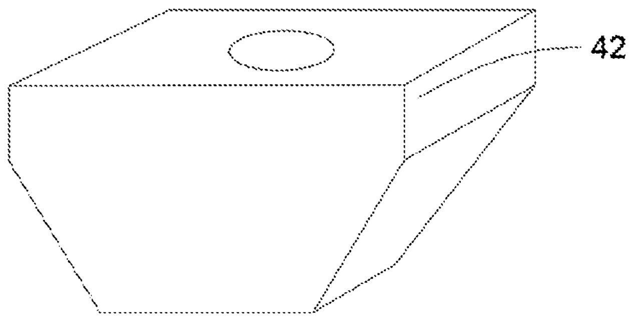
Figure 3E:
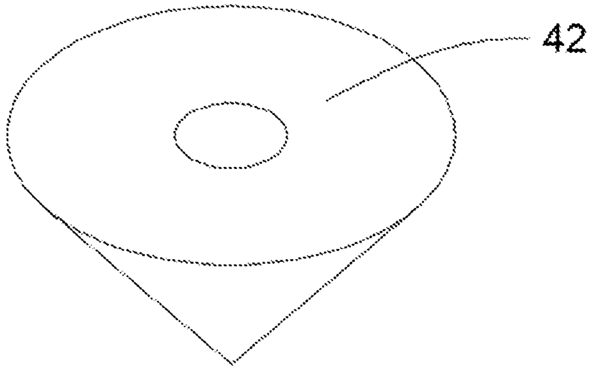
Figure 3F:
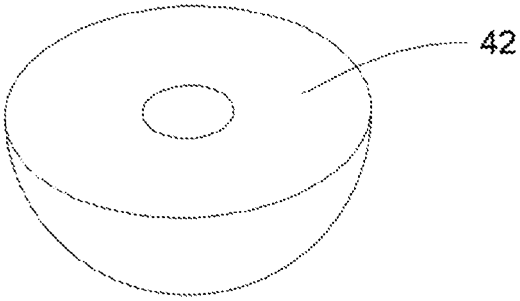
Figure 3G:
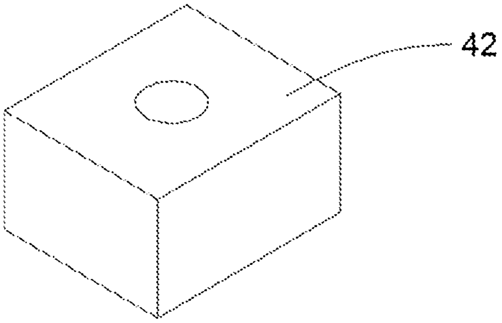

In this embodiment, the self-locking rod 41 is a solid rod, as shown in FIG. 3B. The advantage of this is that it enhances the strength of the inner catheter 4 and prevents the valve clamp 8 from breaking between the detachable connection mechanism of the inner catheter 4 and the releasable connection mechanism on the first delivery catheter 61 during the locking process, resulting in locking failure.

In this embodiment, the cross-section of the locking head 42 in the axial direction is in a wedge-shaped structure, conical structure, trapezoidal structure, or other shape, as shown in FIGS. 3C-3G.

Figure 1D:
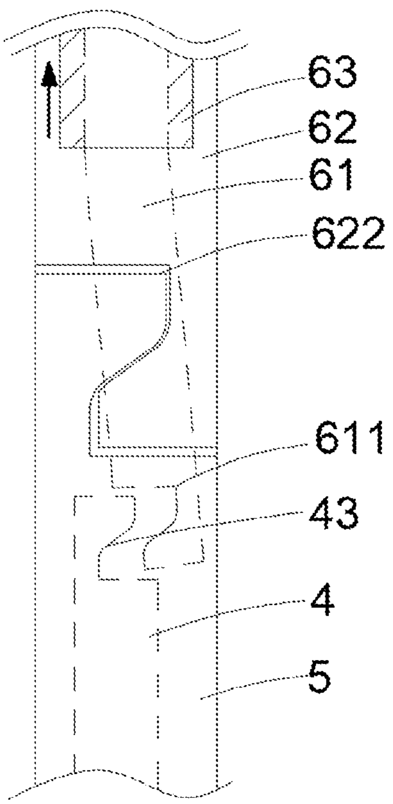
Figure 1E:
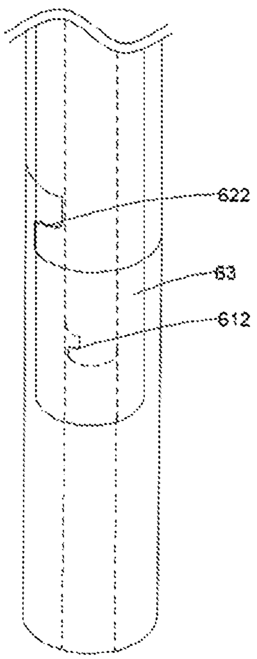
Figure 7A:
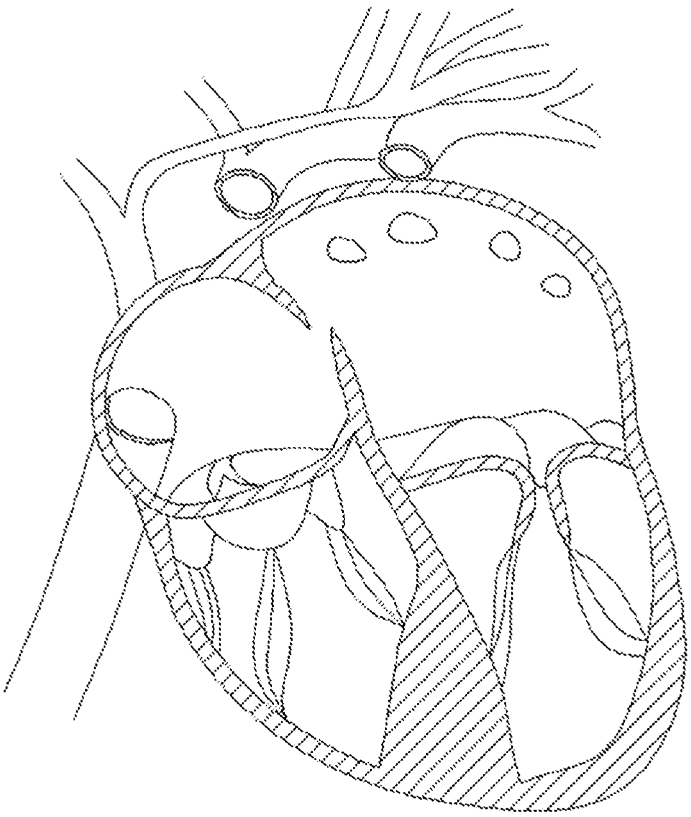
FIGS. 7A-7G are schematic diagrams illustrating the process of the delivery catheter entering a heart of the present application.
Figure 7B:
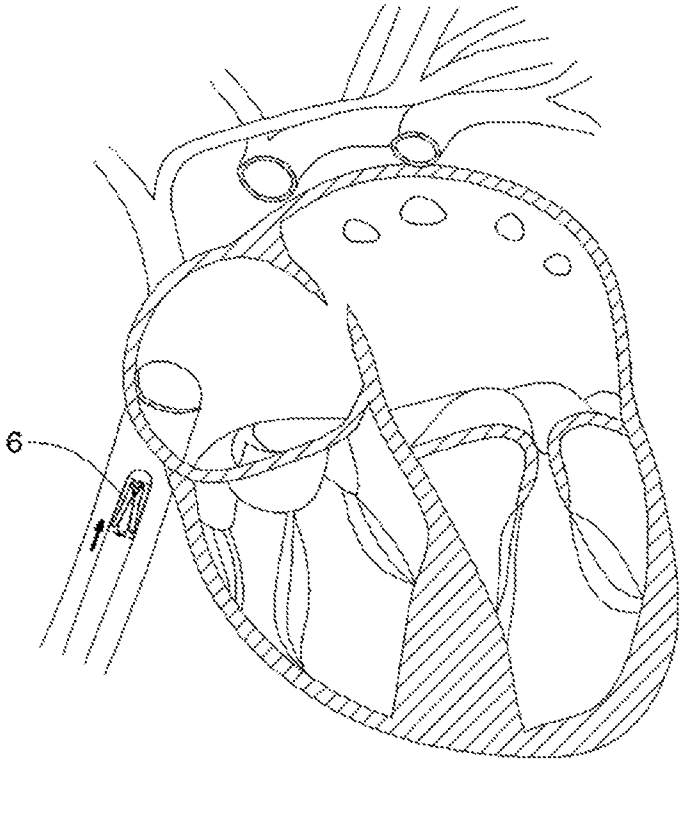
Figure 7C:
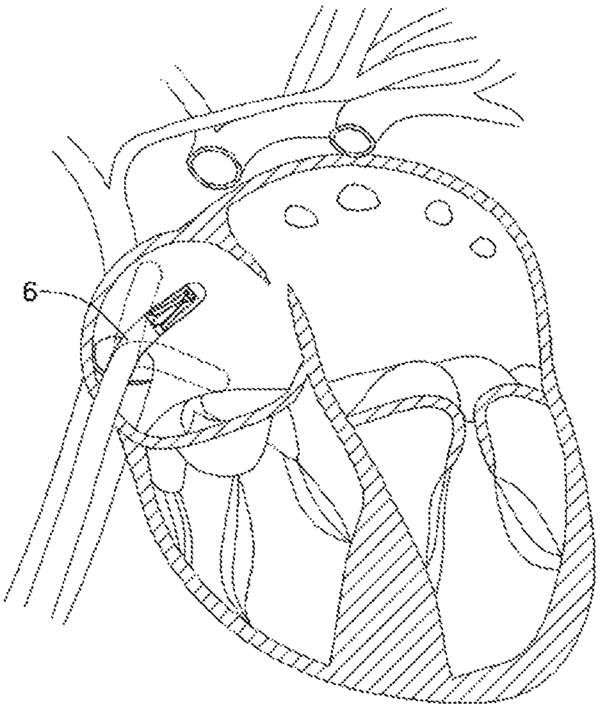
Figure 7D:
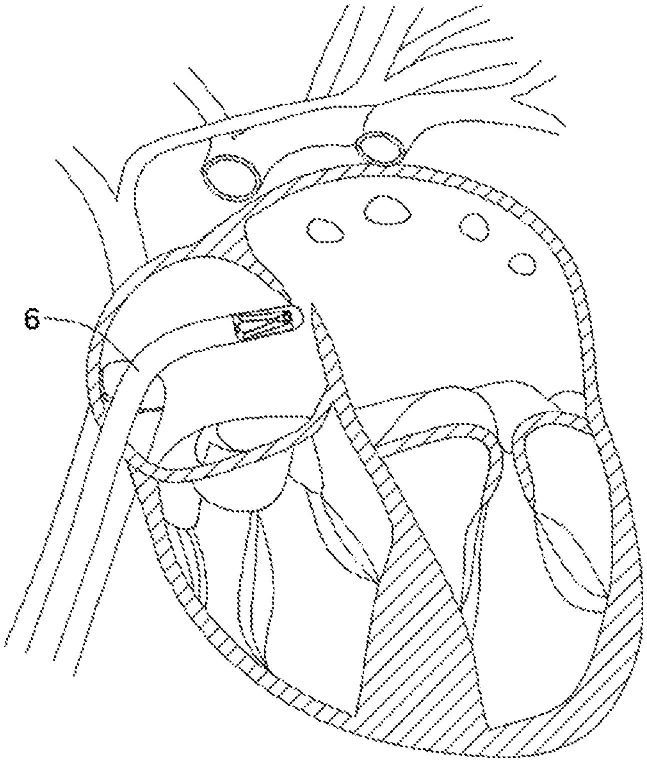
Figure 7E:
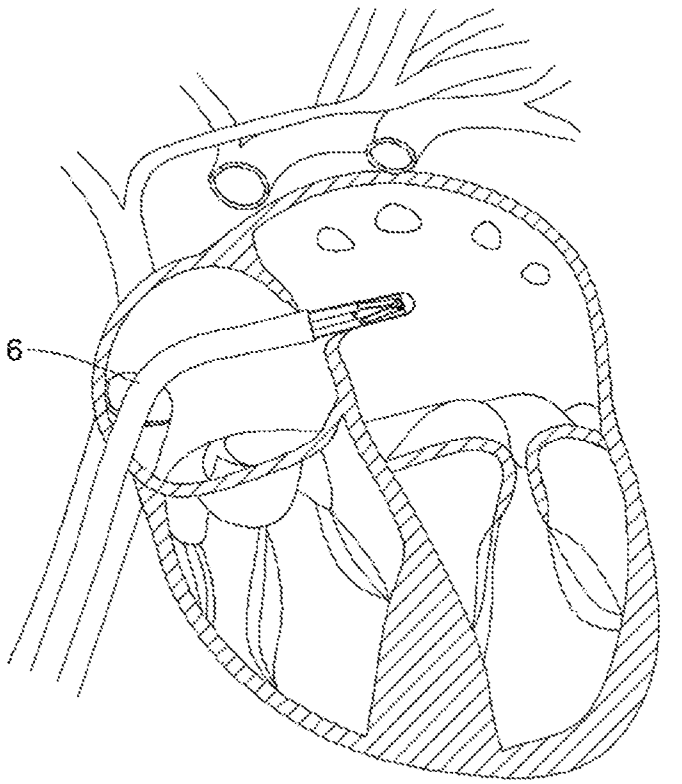
Figure 7F:
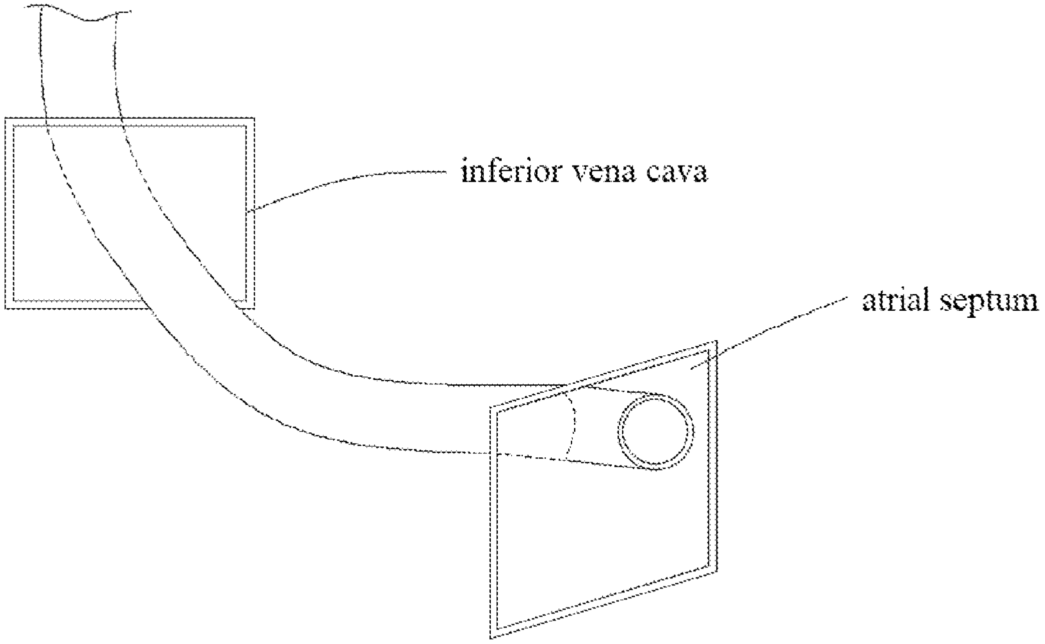
Figure 7G:
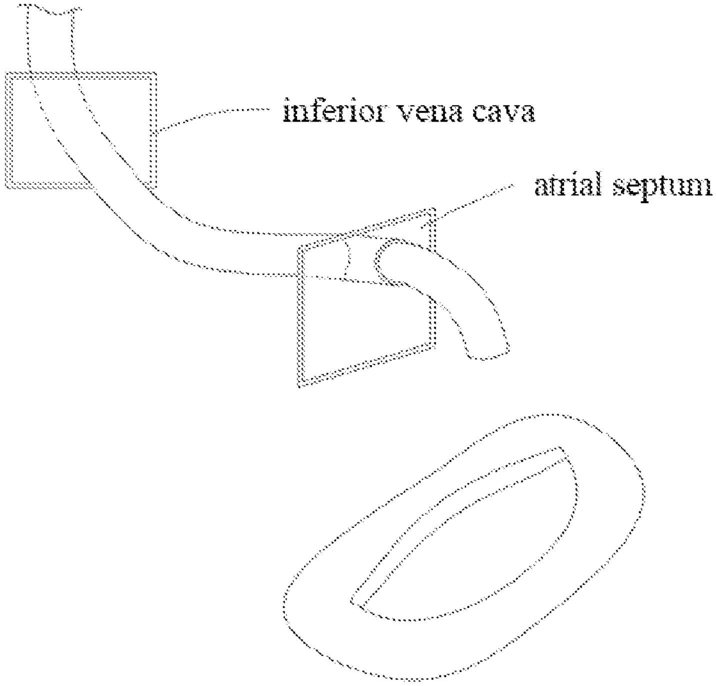
Figure 8A:
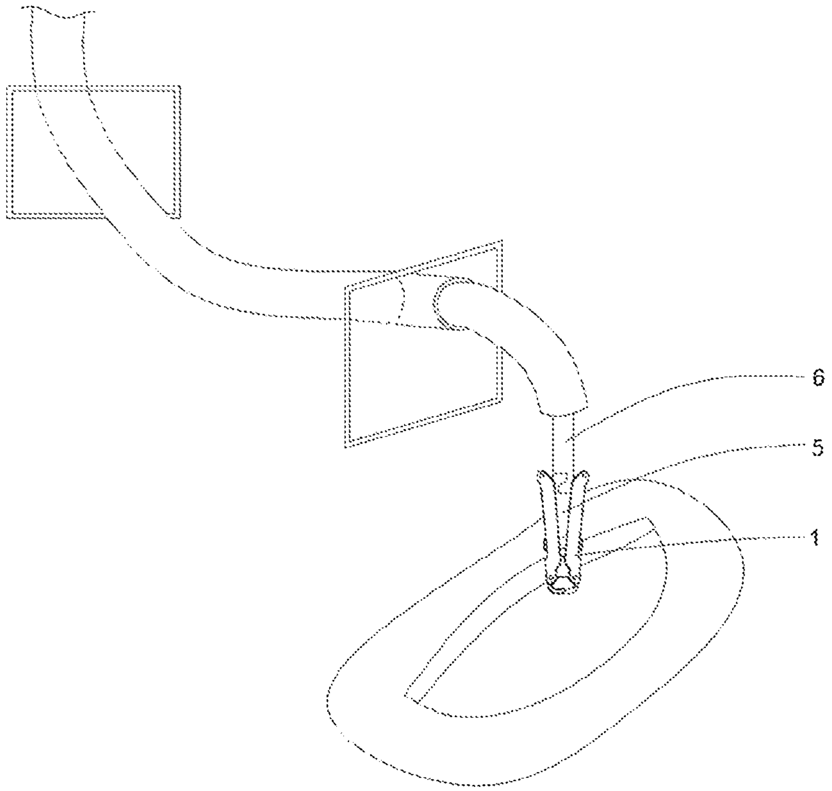
FIGS. 8A-8C are schematic diagrams illustrating the process of opening the valve clamp in a left atrium of the present application.
Figure 8B:
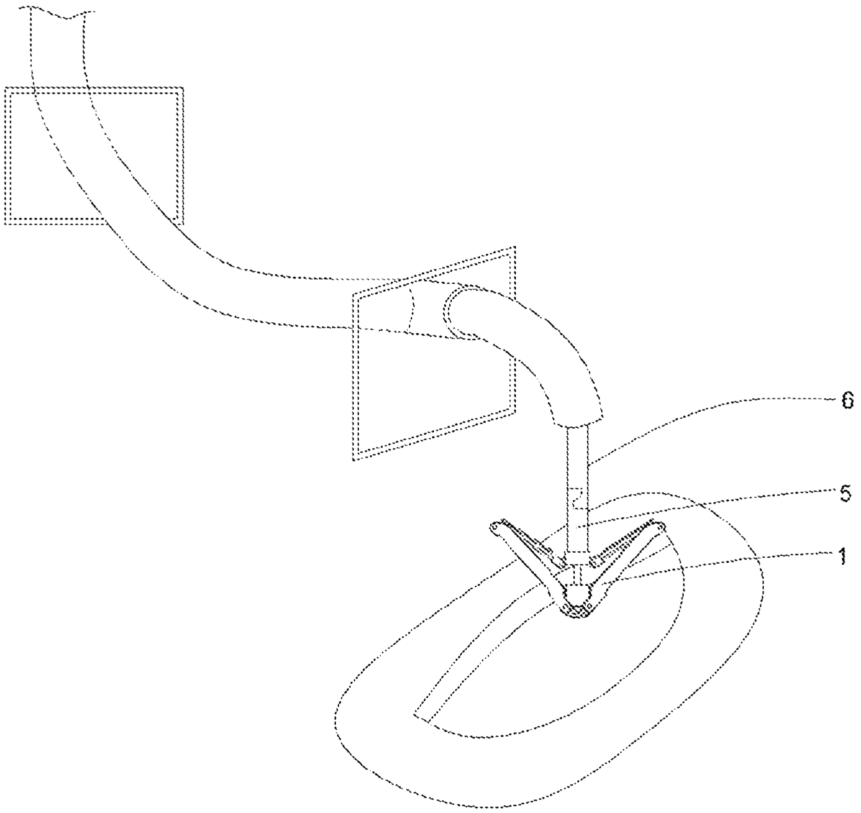
Figure 8C:
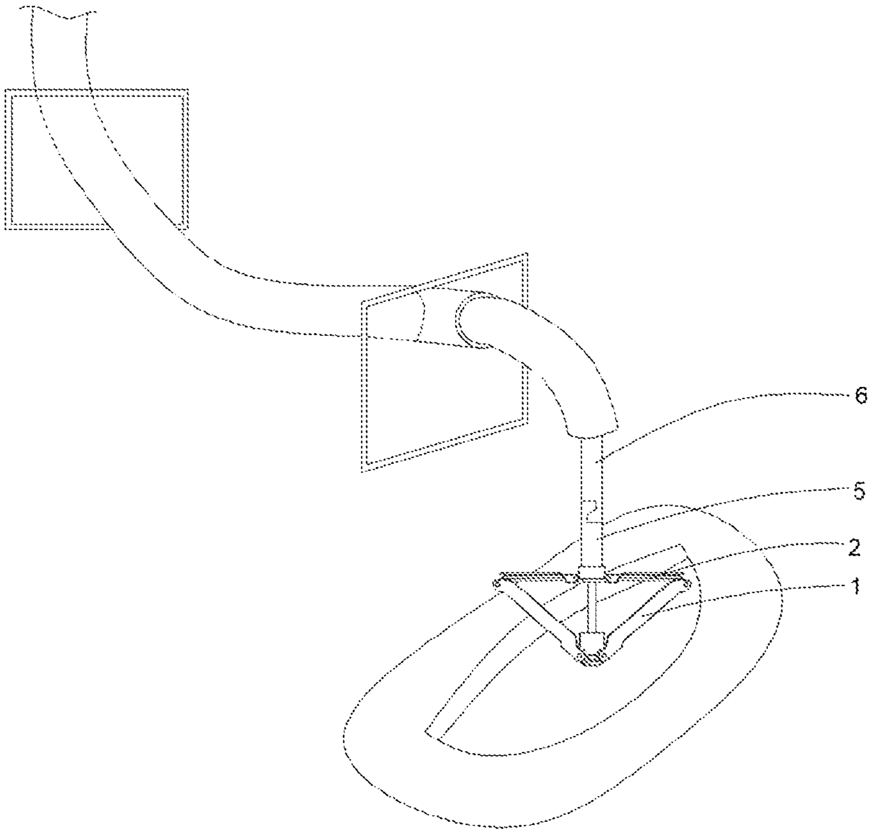
Figure 9A:
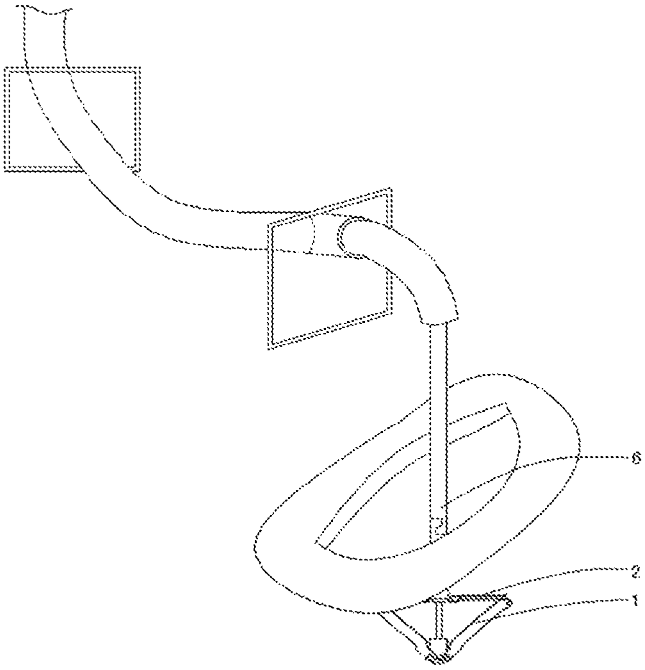
FIGS. 9A-9H are schematic diagrams illustrating the process of the valve clamp of the present application moving to the optimal capturing valve position.
Figure 9B:
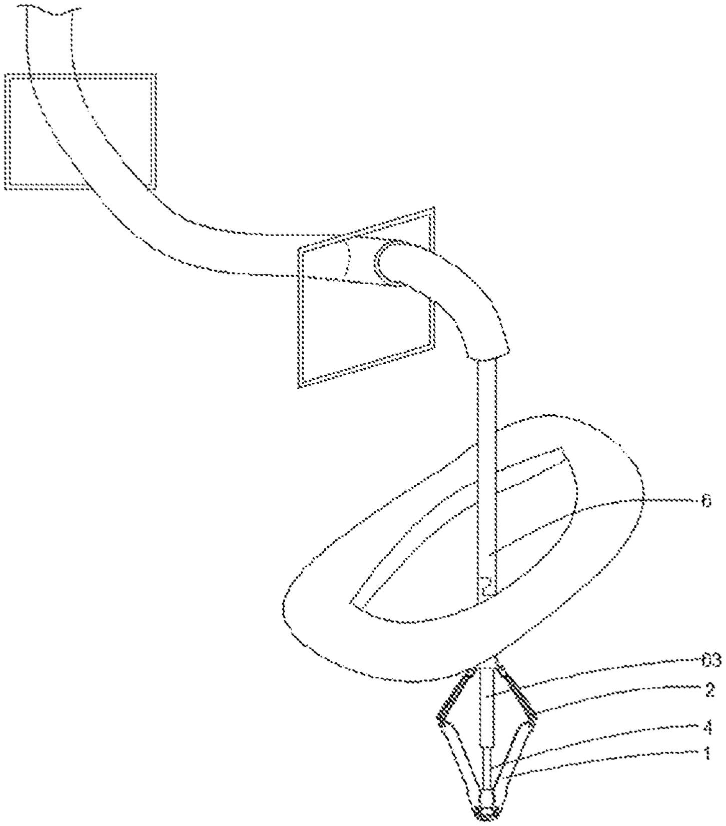
Figure 9C:
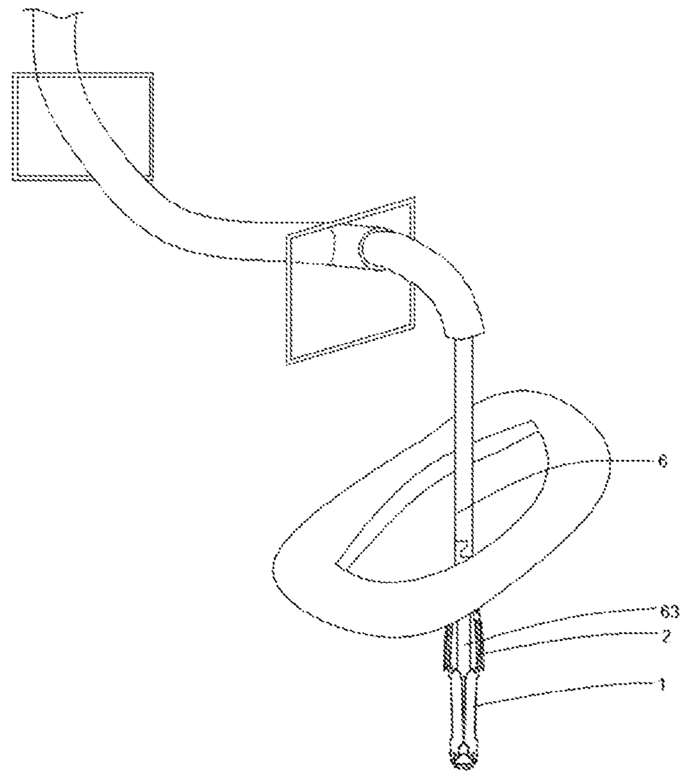
Figure 9D:
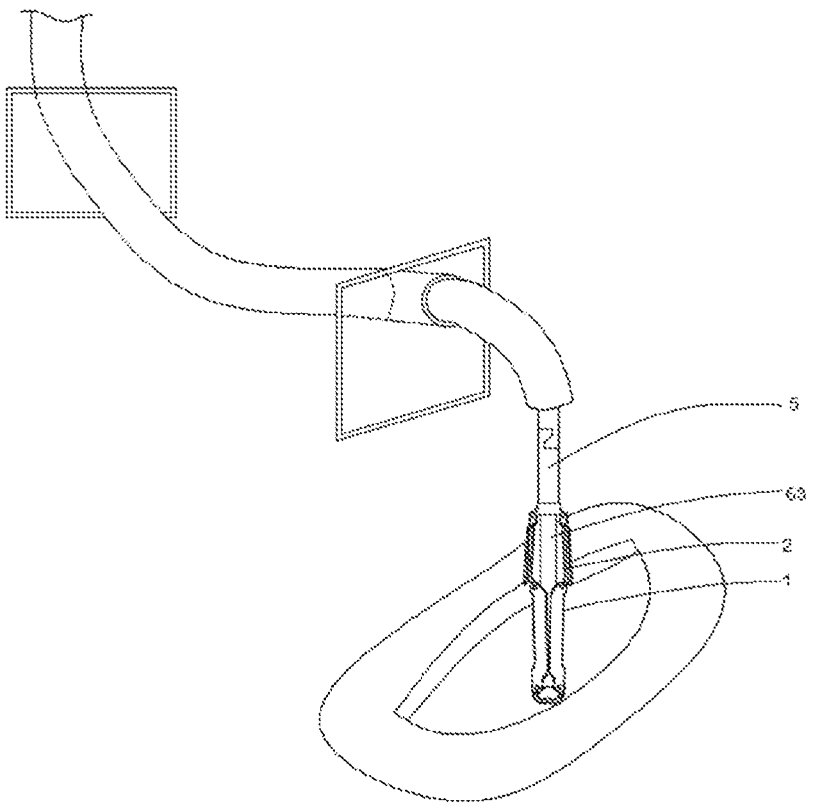
Figure 9E:
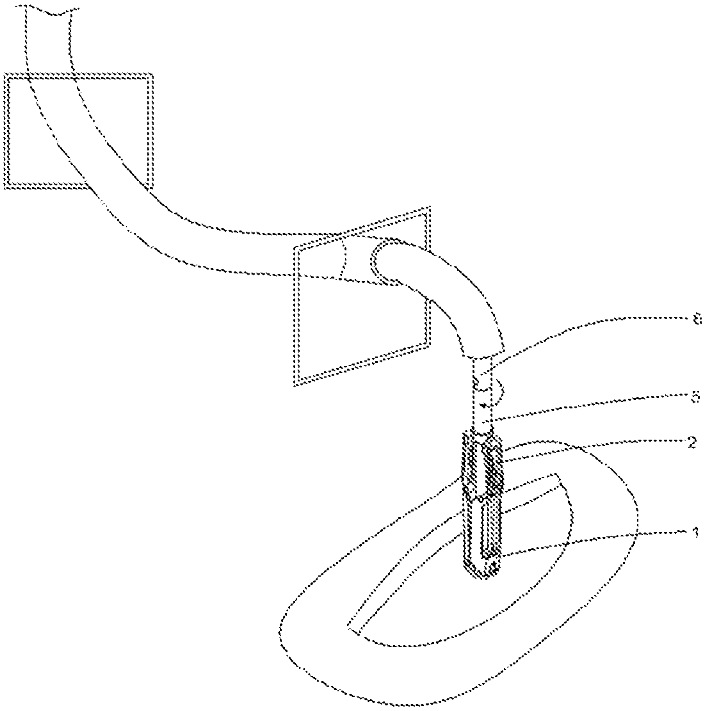
Figure 9F:
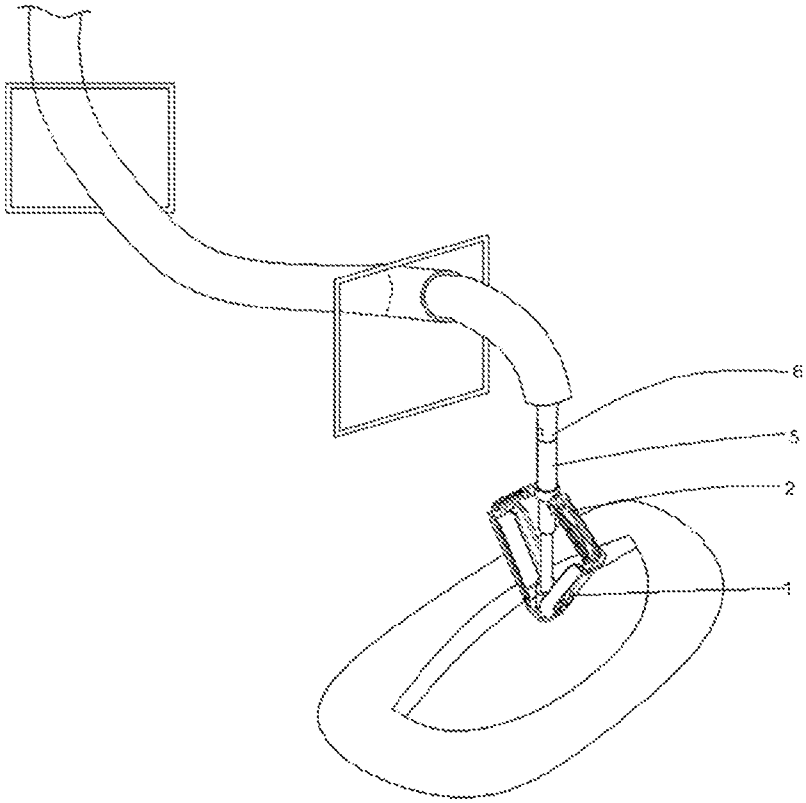
Figure 9G:
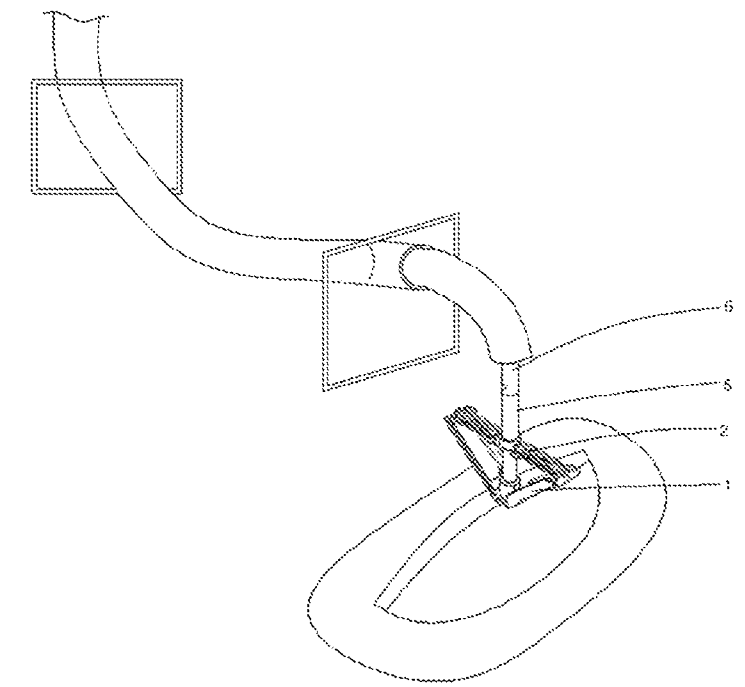
Figure 9H:
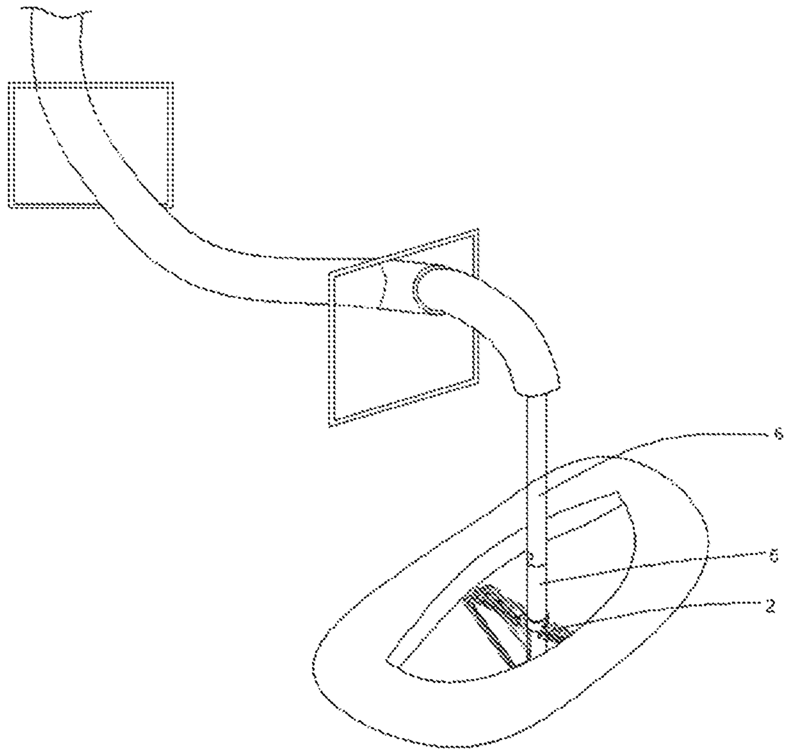

The working principle of the present application is as follows:

1. Operate the valve clamp delivery catheter 6 to enter the heart from the inferior vena cava, and then operate the delivery catheter 6 to make the valve clamp pass through the atrial septum, as shown in FIGS. 7A to 7E; continue to operate the delivery catheter 6 and to bend it so that the valve clamp is facing the mitral valve, as shown in FIGS. 7F to 7G;
2. Operate the control handle of the valve delivery catheter 6 to retract the outer sheath and expose the valve clamp inside the left atrium; then operate the control handle to maximize the angle between the first clamping arm 11 and the second clamping arm 12, as shown in FIGS. 8A to 8C;
3. Operate the control handle to pass the valve clamp through the mitral valve, as shown in FIG. 9A; determine whether the valve clamp is in the optimal valve clamping position through imaging; if it is the optimal position, directly follow step 5; if it is not the optimal position, proceed according to step 4;
4. Operate the control handle to pull the valve clamp to the left atrium, as shown in FIGS. 9B-9D; the clamping arm 1 and the linkage rod 2 are at an obtuse angle, which conforms to the physiological structure and will not harm tissues such as the cardiac chordae tendineae; operate the control handle to rotate and transport the valve clamp to the optimal valve clamping position, as shown in FIGS. 9E to 9H;
5. Operate the control handle to retract the linkage rod 2 to the outer catheter 5 until the flap is clamped between the linkage rod 2 and the outer catheter 5;
6. Operate the inner catheter 4 to move axially towards the distal end along the connector 3 until the locking head 42 enters the fixed area 13, achieving the locking of the valve clamp, as shown in FIG. 4F;
7. When operating the central control unit 63 to move towards the proximal end relative to the first delivery catheter 61 and the second delivery catheter 62, the releasable connection mechanisms (referring to the first releasable connection mechanism 611 and the second releasable connection mechanism 621) are separated from the detachable connection mechanisms (referring to the outer detachable connection mechanism 51 and the inner detachable connection mechanism 43), as shown in FIG. 1D.

Embodiment 2

When used for the treatment of mitral valve disease, as shown in FIGS. 1A and 1B, it includes a control handle, a delivery catheter 6 connected to the control handle, and a valve clamp 8 connected to the delivery catheter 6. The valve clamp 8 is equipped with an inner catheter 4 and an outer catheter 5, both of which are equipped with detachable connection mechanisms. The delivery catheter 6 includes a first delivery catheter 61, a central control unit 63, and a second delivery catheter 62. The distal parts of both the first delivery catheter 61 and the second delivery catheter 62 are equipped with releasable connection mechanisms that match the detachable connection mechanisms. When pre-installed, an inner detachable connection mechanism 43 on the inner catheter 4 is connected to a first releasable connection mechanism 611 on the first delivery catheter 61 through the central control unit 63, forming a first disassembly part 612. An outer detachable connection mechanism 51 on the outer catheter 5 is connected to a second releasable connection mechanism 621 on the second delivery catheter 62 through the central control unit 63, forming a second disassembly part 622. When the central control unit 63 is moved away from the first disassembly part 612 and the second disassembly part 622, the first delivery catheter 61 is separated from the inner catheter 4, and the second delivery catheter 62 is separated from the outer catheter 5.

Figure 6A:
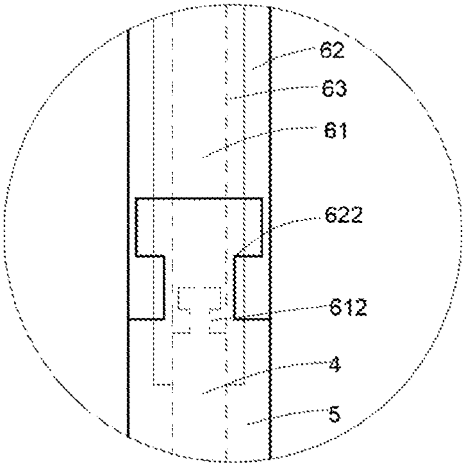
FIGS. 6A-6H illustrate another embodiment of the valve clamp integrated disassembly of the present application.
Figure 6B:
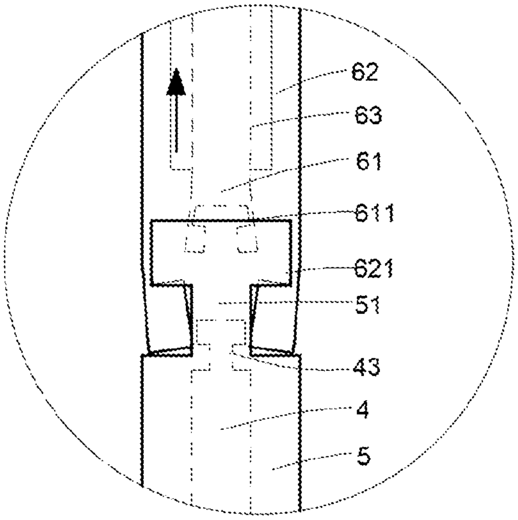
Figure 6C:
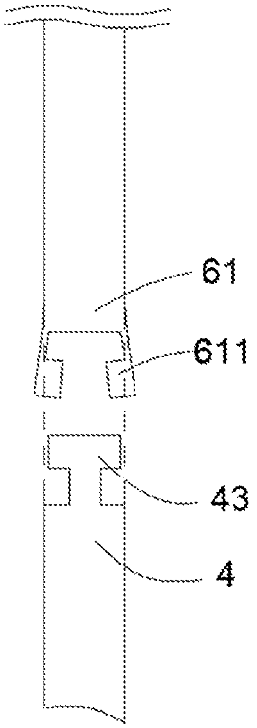
Figure 6D:
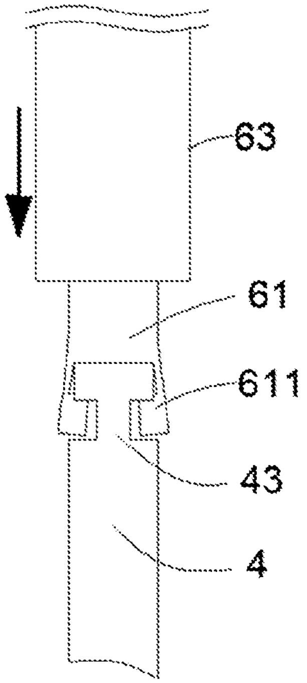
Figure 6E:
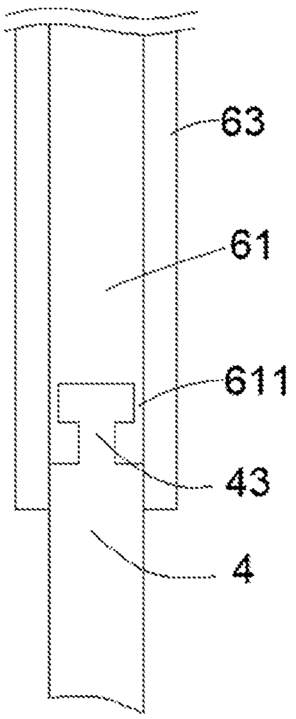
Figure 6F:
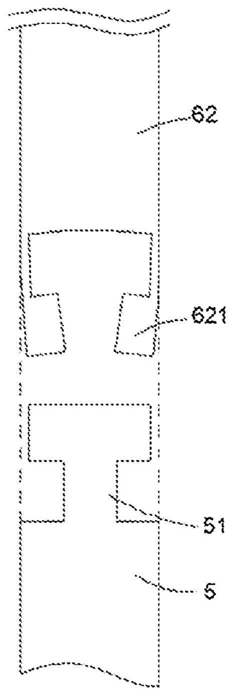

In this embodiment, in a natural state, the outer diameter of a releasable connection mechanism on the first delivery catheter 61 is greater than the outer diameter of detachable connection mechanism on the inner catheter (as shown in FIG. 6C), and the outer diameter of a releasable connection mechanism on the second delivery catheter 62 is smaller than the outer diameter of a detachable connection mechanism on the outer catheter 5 (as shown in FIG. 6F). When the central control unit 63 is between the first delivery catheter 61 and the second delivery catheter 62, the first delivery catheter 61 is compressed by the central control unit 63 to form a detachable connection between the releasable connection mechanism on the first delivery catheter 61 and an inner detachable connection mechanism 43 on the inner catheter 4, and the second delivery catheter 62 is opened by the central control unit 63 to form a detachable connection between the releasable connection mechanism on the second delivery catheter 62 and an outer detachable connection mechanism 51 on the outer catheter 5 (as shown in FIGS. 6C-6H); when the central control unit 63 moves towards the proximal end relative to the first delivery catheter 61 and the second delivery catheter 62, the releasable connection mechanism of the first delivery catheter 61 expands to the original form, and the releasable connection mechanism of the second delivery catheter 62 retracts to the original form, and the releasable connection mechanisms are separated from the detachable connection mechanisms (as shown in FIG. 6B).

In this embodiment, the first releasable connection mechanism 611 is compressed by the central control unit 63 to form a detachable connection with the inner detachable connection mechanism 43. The outer diameter of the first releasable connection mechanism 611 is equal to the outer diameter of the inner detachable connection mechanism 43, and the surface of the first releasable connection mechanism 611 is cylindrical after meshing and connecting with the inner detachable connection mechanism 43, as shown in FIGS. 6C-6E.

Figure 6G:
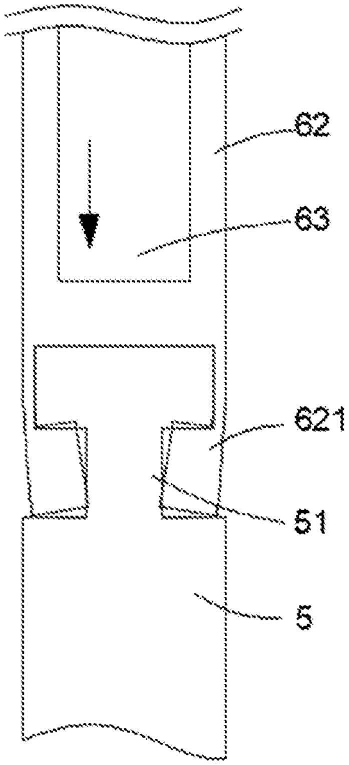
Figure 6H:
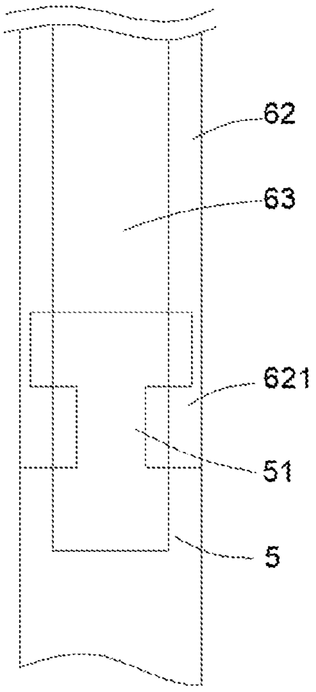

In this embodiment, the second releasable connection mechanism 621 is supported by the central control unit 63 to form a detachable connection with the outer detachable connection mechanism 51. The outer diameter of the second releasable connection mechanism 621 is equal to the outer diameter of the outer detachable connection mechanism 51. The surface of the second releasable connection mechanism 621 is cylindrical after meshing and connecting with the outer detachable connection mechanism 51, as shown in FIGS. 6F to 6H.

In this embodiment, the valve clamp 8 further includes a connector 3, a first clamping arm 11, a second clamping arm 12, a first linkage rod 21, and a second linkage rod 22. The first clamping arm 11 and the second clamping arm 12 are hinged with the connector 3 and are arranged on the left and right sides of the outer catheter 5. The connector 3 is connected to the inner catheter 4. One end of the first linkage rod 21 is connected to the first clamping arm 11, while the other end of the first linkage rod 21 is connected to the outer catheter 5. One end of the second linkage rod 22 is connected to the second clamping arm 12, while the other end of the second linkage rod 22 is connected to the outer catheter 5.

In this embodiment, the inner catheter 4 includes a self-locking rod 41 and a locking head 42 connected to the connector 3 (as shown in FIG. 3A). The clamping arm includes a long arm 14 and a short arm 15 (as shown in FIG. 4C), and one end of the short arm 15 is provided with a first locking part 111 (as shown in FIG. 4D). When the inner catheter 4 is axially moved to enlarge the angle between the long arm 14 of the first clamping arm 11 and the long arm 14 of the second clamping arm 12 to an open state, the first locking part 111 on the first clamping arm 11 and the second locking part 121 on the second clamping arm 12 are in a staggered fit state (as shown in FIGS. 4A and 4B). When the outer catheter 5 is moved axially along the inner catheter 4 to reduce the angle between the long arm 14 of the first clamping arm 11 and the long arm 14 of the second clamping arm 12 to a closed state (as shown in FIG. 4E), the self-locking rod 41 is moved to achieve matching and locking between the locking head 42 and the locking parts (referring to the first locking part 111 and the second locking part 121) (as shown in FIG. 4F). By utilizing the lever principle, a torque balance is generated between the locking head 42 and the locking parts (referring to the first locking part 111 and the second locking part 121), controlling the angle between the first clamping arm 11 and the second clamping arm 12 to no longer increase, achieving the locking effect. Meanwhile, the locking structure is mechanically locked, with a simple structure, easy operation, and no risk of fatigue, which can ensure its clamping effect for a long time.

In this embodiment, a fixed area 13 is formed between the locking parts (referring to the first locking part 111 and the second locking part 121) and the connector 3, and the locking head 42 enters the fixed area 13 and completes a locking fit with the locking parts (referring to the first locking part 111 and the second locking part 121).

In this embodiment, the locking head 42 corresponds to the fixed area 13 in a wedge-shaped structure, conical structure, trapezoidal structure, or other shape.

The above descriptions are merely preferable embodiments of the present application. For those of ordinary skill in the art, according to the idea of the present application, there will be changes in the specific embodiments and application. The content of this specification should not be understood as a limitation of the present application.

What is claimed is:

1. A component of an integrally detachable valve clamp and delivery system thereof, comprising:
- a control handle;
- a delivery catheter connected to the control handle; and
- a valve clamp connected to the delivery catheter;
- wherein the valve clamp is equipped with an inner catheter and an outer catheter, both of which are equipped with detachable connection mechanisms; the delivery catheter comprises a first delivery catheter, a central control unit, and a second delivery catheter; the distal parts of both the first delivery catheter and the second delivery catheter are equipped with releasable connection mechanisms that match the detachable connection mechanisms;
- when pre-installed, the detachable connection mechanism on the inner catheter is connected to the releasable connection mechanism on the first delivery catheter through the central control unit, forming a first disassembly part, while the detachable connection mechanism on the outer catheter is connected to the releasable connection mechanism on the second delivery catheter through the central control unit, forming a second disassembly part; when the central control unit is moved away from the first disassembly part and the second disassembly part, the first delivery catheter separates from the inner catheter, and the second delivery catheter separates from the outer catheter.

2. The component of an integrally detachable valve clamp and delivery system thereof according to claim 1, wherein the relative position of the central control unit and the inner catheter remains unchanged when the first disassembly part and the second disassembly part undergo relative displacement.

3. The component of an integrally detachable valve clamp and delivery system thereof according to claim 1, wherein on the axial section of the delivery catheter, the first disassembly part and the second disassembly part are in the same or different positions, and when the central control unit is moved away from the first and second disassembly parts respectively/simultaneously, the first delivery catheter and the inner catheter, the second delivery catheter and the outer catheter are correspondingly released and separated in sequence/simultaneously.

4. The component of an integrally detachable valve clamp and delivery system thereof according to claim 1, wherein the valve clamp further comprises a connector, a first clamping arm, a second clamping arm, a first linkage rod, and a second linkage rod; the first clamping arm and the second clamping arm are hinged with the connector and are arranged on the left and right sides of the outer catheter; the connector is connected to the inner catheter; one end of the first linkage rod is connected to the first clamping arm, while the other end of the first linkage rod is connected to the outer catheter; and one end of the second linkage rod is connected to the second clamping arm, while the other end of the second linkage rod is connected to the outer catheter.

5. The component of an integrally detachable valve clamp and delivery system thereof according to claim 1, wherein the central control unit restricts the relative radial displacement between the detachable connection mechanisms and the releasable connection mechanisms to prevent the detachable connection mechanisms from detaching from the releasable connection mechanisms.

6. The component of an integrally detachable valve clamp and delivery system thereof according to claim 1, wherein each of the detachable connection mechanisms comprises a first connection section, a second connection section, and an inclined section, and the inclined section is set between the first connection section and the second connection section.

7. The component of an integrally detachable valve clamp and delivery system thereof according to claim 6, wherein the central control unit is a tube, the wall thickness of which is greater than or equal to half of the radial distance between the first connection section and the second connection section on the detachable connection mechanism of the inner catheter.

8. The component of an integrally detachable valve clamp and delivery system thereof according to claim 1, wherein when the releasable connection mechanisms are connected to the detachable connection mechanisms through the central control unit, the first delivery catheter and the second delivery catheter can respectively transmit torque and push force to the inner catheter and the outer catheter.

9. The component of an integrally detachable valve clamp and delivery system thereof according to claim 4, wherein the inner catheter comprises a self-locking rod and a locking head connected to the connector; the first clamping arm and the second clamping arm respectively comprises a long arm and a short arm, and one end of the short arm is provided with a locking part; when the inner catheter is axially moved to enlarge the angle between the long arm of the first clamping arm and the long arm of the second clamping arm to an open state, the locking part on the first clamping arm and the locking part on the second clamping arm are in a staggered fit state; when the inner catheter is moved axially to reduce the angle between the long arm of the first clamping arm and the long arm of the second clamping arm to a closed state, the self-locking rod is moved to achieve matching and locking between the locking head and the locking part.

10. The component of an integrally detachable valve clamp and delivery system thereof according to claim 9, wherein the locking head is a bracket shaped self-expanding structure, which cooperates with the locking part to achieve locking.

* * * * *